(12) United States Patent
Hui (10) Patent No.: US 8,651,110 B2
(45) Date of Patent: *Feb. 18, 2014

(54) LUBRICATED CONDOM

(71) Applicant: Lap Shun Hui, Long Beach, CA (US)

(72) Inventor: Lap Shun Hui, Long Beach, CA (US)

(*) Notice: Subject to any disclaimer, the term of this patent is extended or adjusted under 35 U.S.C. 154(b) by 9 days.

This patent is subject to a terminal disclaimer.

(21) Appl. No.: 13/721,602

(22) Filed: Dec. 20, 2012

(65) Prior Publication Data

US 2013/0104904 A1    May 2, 2013

Related U.S. Application Data (63) Continuation-in-part of application No. 12/951,469, filed on Nov. 22, 2010, now Pat. No. 8,443,809, which is a continuation-in-part of application No. 12/842,252, filed on Jul. 23, 2010, now abandoned, which is a continuation-in-part of application No. 12/454,907, filed on May 26, 2009, now abandoned.

(60) Provisional application No. 61/103,601, filed on Oct. 8, 2008, provisional application No. 61/114,503, filed on Nov. 14, 2008.

(51) Int. Cl.
```
A61F 6/02      (2006.01)
A61F 6/04      (2006.01)
A61F 5/44      (2006.01)
A41D 19/00     (2006.01)
B05D 3/00      (2006.01)
```

(52) U.S. Cl.
USPC ............ 128/844; 128/842; 128/918; 427/2.3; 604/346; 604/347; 604/349; 604/350

(58) Field of Classification Search
USPC ........ 128/842, 844, 918; 427/2.3; 600/38–41; 604/346–353
See application file for complete search history.

(56) References Cited

U.S. PATENT DOCUMENTS

| | | | | |
|---|---|---|---|---|
| 4,919,149 A | * | 4/1990 | Stang | 128/842 |
| 5,626,149 A | * | 5/1997 | Schwartz | 128/842 |
| 2006/0081264 A1 | * | 4/2006 | Vera | 128/884 |

* cited by examiner

*Primary Examiner* — Patricia Bianco
*Assistant Examiner* — Brandon L Jackson
(74) *Attorney, Agent, or Firm* — Lance M. Pritikin, Esq.; Wolf, Rifkin, Shapiro, Schulman & Rabkin, LLP (57) ABSTRACT

A condom, including a non-porous sheath member, having an open end and a rounded end, and shaped to cover the glans and body portion of a penis, and at least one rib having at least one outer portion and at least one inner portion, wherein the at least one outer portion is attachedly fixed to said non-porous sheath member, and wherein an inner cylinder formed by at the at least one inner portion is exclusive from said non-porous sheath member, and including at least one lubricant within the inner cylinder and at least one hole extending from the inner cylinder through the outer portion to provide for flow of the lubricant outwardly from the inner cylinder through the at least one hole pursuant to application of a predetermined pressure, wherein the at least one rib extends at least one of substantially from the open end to the closed end and substantially about a circumference of the non-porous sheath member.

5 Claims, 13 Drawing Sheets

LUBRICATED CONDOM

CROSS-REFERENCE TO RELATED APPLICATIONS

This application is a continuation of U.S. patent application Ser. No. 12/951,469 filed Nov. 15, 2011, now pending, which is a continuation-in-part of application Ser. No. 12/842,252, filed on Jul. 23, 2010, now abandoned, which is a continuation-in-part of application Ser. No. 12/454,907, filed on May 26, 2009, now abandoned, which claims the benefit of Provisional Application No. 61/103,601, filed on Oct. 8, 2008, and Provisional Application No. 61/114,503, filed on Nov. 14, 2008. The entire contents of each of the aforementioned applications are incorporated herein by this reference for all purposes as if fully set forth herein.

FIELD OF THE INVENTION

The present invention is directed generally to a method and apparatus for providing lubrication and, more particularly, to a lubricated condom.

BACKGROUND OF THE INVENTION

Sanitary contraceptives, such as condoms, are primarily designed to prevent the transfer of disease and unwanted pregnancy. Condoms have also been designed to provided stimulation through mechanical, chemical and visual means. Ribbed condoms that glow in the dark may provide both a mechanical an visual stimulation, for example. Further, use of external lubricants have been employed to increase satisfaction and ease of use for both the user of the condom and the user's partner.

However, the lubrications employed historically fail to provide a sufficient amount of lubricant, and fail to provide lubrication in a timely manner. If a lubricant is only provided at the initiation of use, the lubricating effects of the provided lubricant may diminish such that no practical lubrication is provided by the condom for a period of time before use ends. This may cause irritation for the users of the condom and may cause the condom to become dislodged.

Thus, there exists a need for a condom which can provide lubrication semi-continuously and/or as desired during use, rather than providing only a limited of lubricant prior to use.

SUMMARY OF THE INVENTION

The present invention is directed to a condom, including a non-porous sheath member, having an open end and a rounded end, and shaped to cover the glans and body portion of a penis, and at least one rib having at least one outer portion and at least one inner portion, wherein the at least one outer portion is attachedly fixed to said non-porous sheath member, and wherein an inner cylinder formed by at the at least one inner portion is exclusive from said non-porous sheath member, and including at least one lubricant within the inner cylinder and at least one hole extending from the inner cylinder through the outer portion to provide for flow of the lubricant outwardly from the inner cylinder through the at least one hole pursuant to application of a predetermined pressure, wherein the at least one rib extends at least one of substantially from the open end to the closed end and substantially about a circumference of the non-porous sheath member.

The present invention solves problems experienced with the prior art because it provides lubrication semi-continuously, and on-demand, during use. Those and other advantages and benefits of the present invention will become apparent from the detailed description of the invention hereinbelow.

BRIEF DESCRIPTION OF THE FIGURES

The present invention will be described hereinbelow in conjunction with the following figures, in which like numerals represent like items, and wherein.

DETAILED DESCRIPTION OF THE INVENTION

It is to be understood that the figures and descriptions of the present invention have been simplified to illustrate elements that are relevant for a clear understanding of the present invention, while eliminating, for purposes of clarity, many other elements found in typical condoms. Those of ordinary skill in the art will recognize that other elements are desirable and/or required in order to implement the present invention. However, because such elements are well known in the art, and because they do not facilitate a better understanding of the present invention, a discussion of such elements is not provided herein.

Figure 1:
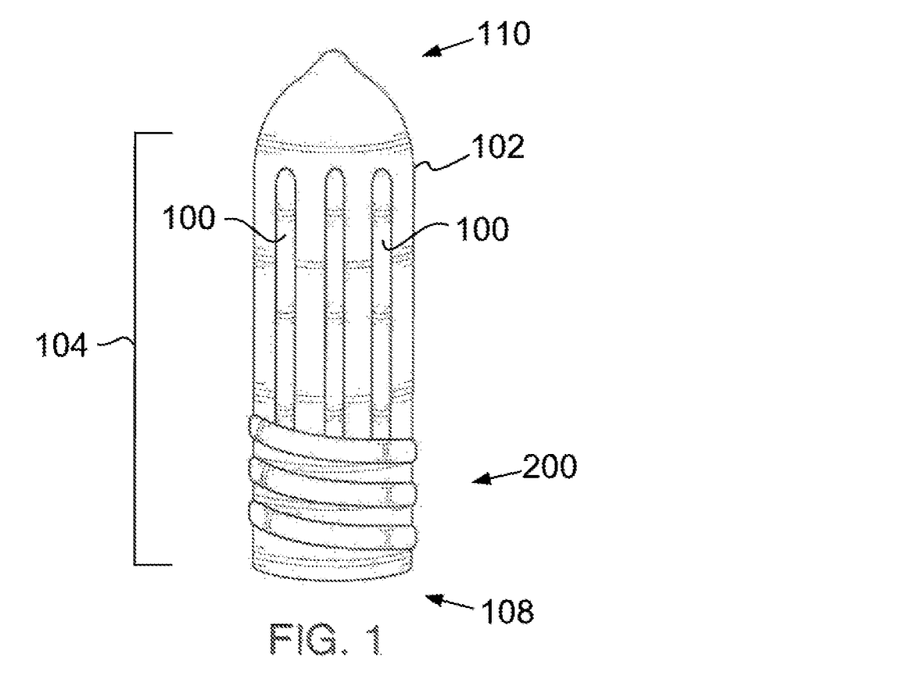
FIG. 1 illustrates an exemplary embodiment of the present invention.

FIG. 1 illustrates a condom in accordance with the present invention. As illustrated, the condom may include two or more ribs 100 along the barrel of the condom. Such ribs may be integral to, or separate from, the length of the barrel of the condom, but in a preferred embodiment, the underlying aspects of the condom are to remain intact, watertight, and free of holes, irrespective of any holes, openings, veins, bladders, or the like integral with the aforementioned ribs of the present invention.

As used herein, the term "ribs" includes any vein, bladder, pathway, or the like, extending along any portion of the length of the barrel of a condom. As such, a rib, as used herein, provides a path for the flow of lubricant in at least a partially substantially parallel direction to the barrel of the condom, although, in certain embodiments, such flow along a rib may additionally occur along a portion substantially perpendicular to the length of the barrel of the condom.

Figure 2:
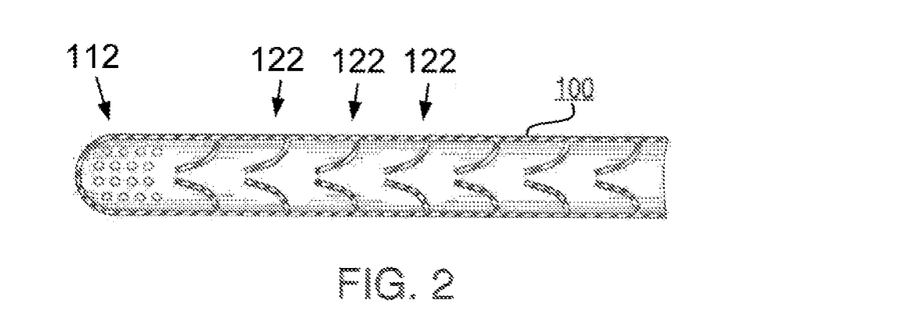
FIG. 2 illustrates a cross-section of at least one rib.
Figure 3:
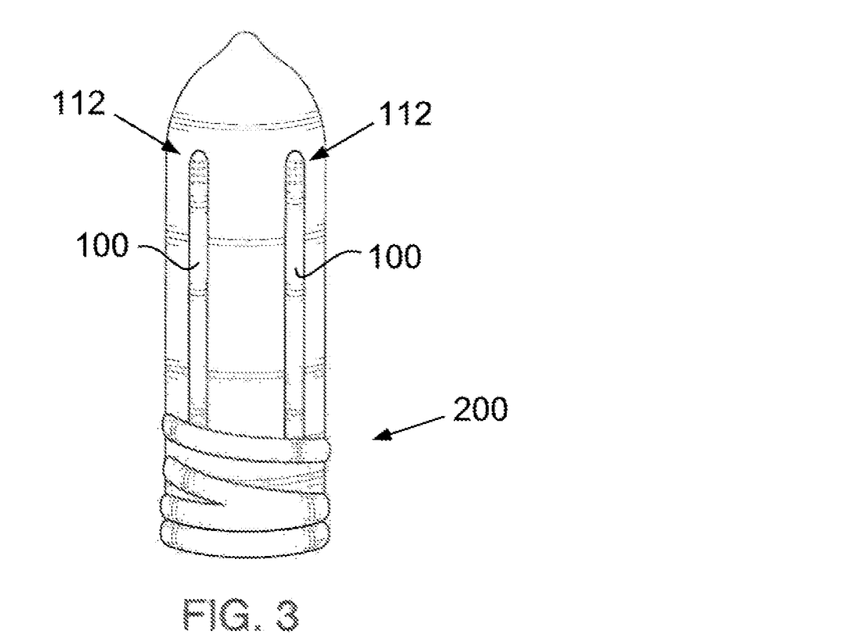
FIG. 3 illustrates an exemplary embodiment of the present invention.

As illustrated for example in FIGS. 1 and 3, a non-porous sheath member 102 may extend between an open end 108 and a closed end 110. Further, ribs 100 may extend along the barrel 104, for example, generally longitudinally from the open end 108 toward the closed end 110. As more particularly illustrated in FIG. 2, a rib may allow for a flow of lubricant along or around the barrel 104 of the condom. Such flow of lubricant may, in certain preferred embodiments, be directional, i.e., one way, at least in that the rib may include veins, valves, bladders, or the like that direct the flow of lubricant, such as upward from the base of the condom toward the tip of the condom during use of the condom. Such ribs 100 may additionally include, such as along the length of the rib 100 or at or near a termination of a rib, an exit pathway 112, such as a valve, hole or holes, that allow lubricant to exit the condom. As illustrated for example in FIG. 2, a multiplicity of unidirectional valve elements 122 may be housed within the rib 100 in serially-distributed fashion for directing the flow of a lubricant within the rib toward the exit pathway 112 and inhibiting flow of the lubricant within the rib away from the exit pathway 112. As discussed hereinabove, and in accordance with the present invention, it almost goes without saying that such valves, holes or exit pathways should in no way interact with, pierce, or otherwise allow leakage from any portion of the underlying body of the condom, thereby preventing any leakage or penile discharge from inside the condom.

As further illustrated in FIG. 3, the ribs of the present invention may provide a pathway at the base of the condom to one or more reservoirs 200 containing the aforementioned lubricant, which may, needless to say, be spermicidal lubricant. As illustrated for example in FIGS. 1 and 3, one or more reservoirs 200 may be affixed to and circumferentially disposed about the barrel, and may also be spiral-shaped. For example, pressure exerted along the barrel of the condom and focused at the base of the condom may force lubricant out of the one or more reservoirs and along the uni-directional ribs outward toward the upper tip of the condom. Thus, a reservoir 200 may contain a lubricant for flow of the lubricant into the ribs 100 by way of fluid communication between the reservoir and the respective ribs. Such reservoirs may simply be one, two, three, or more spirals perpendicularly around the base of the condom, filled with lubricant, and sealed at the end of the reservoir spiral closest to the base of the condom. Thereby, when force is exerted at the base of the condom, the lubricant may, in accordance with a predetermined desired flow rate, flow around the spiral reservoir or reservoirs and upward along the barrel of the condom during use. Similarly, a single reservoir may be placed laterally around or approximate to the base of the condom, and such single reservoir may or may not be connected to the aforementioned spiral ribs, wherein, upon exertion of pressure downward along the barrel of the condom toward the base, pressure is exerted on the lubricant and the lubricant is forced from the reservoir and upward through the aforementioned ribs.

Figure 4:
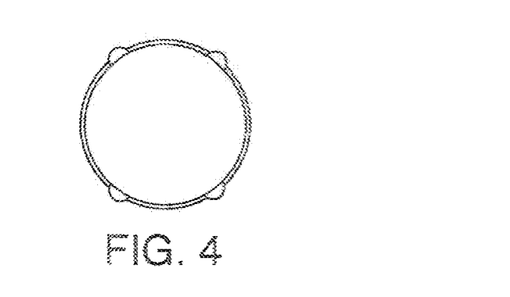
FIG. 4 illustrates a cross-section of the present invention.

More particularly, FIG. 4 illustrates a condom having multiple, discrete reservoirs. As illustrated, the multiple reservoirs may include one or more reservoirs extending latitudinally upward along the sheath of the condom, which latitudinal reservoirs may be connected to a longitudinal reservoir or reservoirs about the base of the condom sheath. Further, FIG. 4 illustrates a discrete longitudinal series of reservoirs, each extending longitudinally around the sheath, and each discrete from at least one other longitudinal reservoir, and from the latitudinal reservoirs.

At present, the use of condoms presents various difficulties remedied by the present invention. For example, in prior art embodiments, lubrication provided on the condom may be providing in quantities greater than necessary in order to provide initial lubrication. Thereby, excess lubrication may reach the inside of the condom, such as when the condom is rolled up, and may thus cause the condom to be loose or difficult to use. This may particularly be the case when, in use, additional lubrication is added to the exterior of the condom. For example, such additional lubrication may simply work its way down to the base of the condom and have little effect during usage. As will be apparent to those skilled in the art in light of the discussion herein, the present invention remedies such issues. For example, the reserve lubrication provided in the present invention may be, in effect, time released, such as based on the presence of veins or valves as discussed herein, and may be released at the position most in need of lubrication during use of the condom, that is, at the tip of the condom. As such, the present invention may be particularly useful in remedying the dryness that typically occurs after longer periods of usage of a condom. Likewise, the time release or targeted release of lubrication in the condom of the present invention may be prevent buildup of lubrication in undesired areas, that is, in those areas that may cause slippage of the condom, or difficulty in unrolling the condom.

Needless to say, the present invention may be provided with multiple reserves of lubricant, such as wherein each reservoir is separately time released, or is subject to release under different pressures, or subject to simultaneous release. Such multiple reservoirs may be used to create, for example, a ribbed effect for additional pleasure during use, as well as providing additional targeted lubricant during the use of the present invention.

Figure 5:
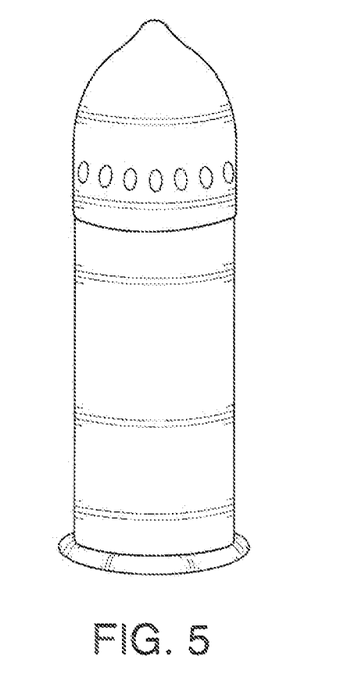
FIG. 5 illustrates a cross-section of the present invention.
Figure 6:
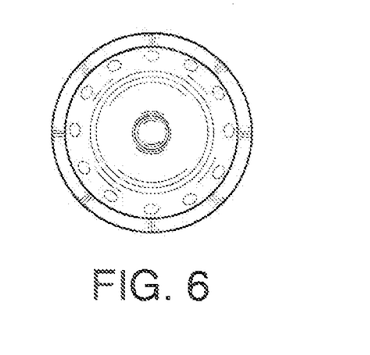
FIG. 6 illustrates a cross-section of the present invention.

In addition to and alternatively to the veins and/or tubular reservoirs for delivering lubricant as discussed hereinabove, FIG. 5 illustrates a cross-sectional view of a condom having an extended spermicidal reservoir tip, as is known in the art, and additionally having a lubricant reservoir above the prior art extended tip. More particularly, FIG. 5 illustrates a condom sheath atop which is a prior art "extended tip", such as for improved containing of the force of an ejaculation, and a lubricant reservoir above or associated with the prior art extended tip. The lubricant discussed herein may be delivered from this upper reservoir. As illustrated in the cross-sectional view of FIG. 6, the reservoir may deliver lubricant via one or more holes, valves, or the like, as discussed above with respect to FIGS. 1-4, and may deliver the lubricant responsive to pressure, breakage, physical removal of impediments to lubricant flow, expansion, or the like.

For example, and particularly with respect to the embodiments illustrated in FIGS. 1, 3, 5-7, and 10-17, the lubricant may be released by a pressure, such as may be applied to the condom by manual squeezing, thrusting with the condom, or the like. Further, breakage of thin seals located, for example, atop the lubricant reservoir of FIGS. 5 and 6, such as by use of the condom or unrolling of the condom, may allow for the release of the lubricant. Yet further, physical removal of, for example, a seal placed on the uppermost portion of the condom, such as while the condom is rolled and/or within its packaging, may be removed in order to allow release of the lubricant. Finally, pressure caused by expansion, such as of the penis within the condom, may effectuate release of the lubricant.

Figure 7:
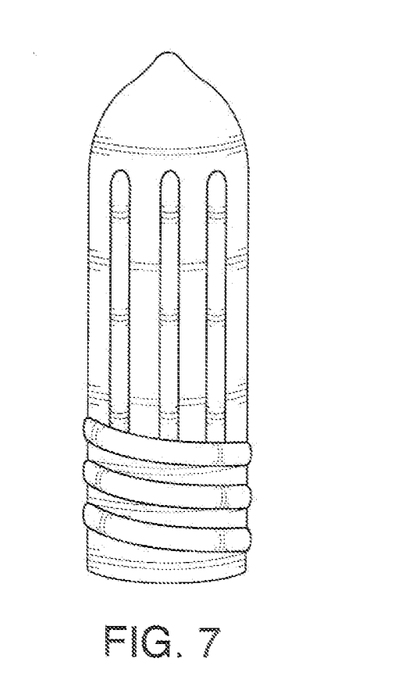
FIG. 7 illustrates a cross-section of the present invention.

FIG. 7 illustrates, in the manner discussed hereinabove, that one or more lubricant reservoir ringed ribs may be placed about the condom. As discussed above, and in preferred embodiments, the lubricant ring ribs may be distinct from the underlying continuous layer of the condom, such that bodily fluids released within the condom cannot leak into the lubricant ring and/or through the lubricant ring to the exterior of the condom. The lubricant ring ribs illustrated in FIG. 7 may remain in an overlapped position as to one another of the multiple ring ribs, such as while the condom is in its rolled and/or packaged configuration.

Figure 8:
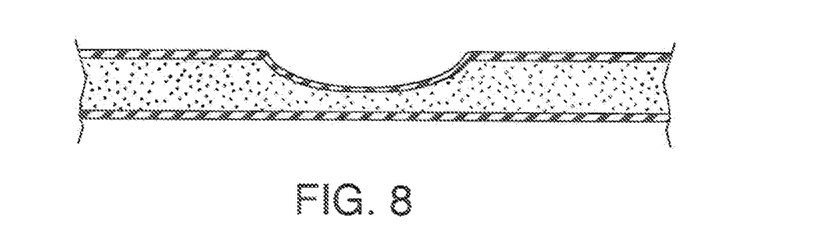
FIG. 8 illustrates a cross-section of a rib and a condom roll in the present invention.

FIG. 8 illustrates a lubricant ring rib of the present invention, wherein the condom roll is peripherally and circumferentially outside the lubricant ring rib in the rolled position. As illustrated, the lubricant ring rib includes at least one hole that is laterally adjacent to the condom roll at the outer periphery of the lubricant ring rib. This at least one hole at the outermost portion of the lubricant ring rib, may, as illustrated in FIG. 8, be plugged prior to unrolling of the condom. Such a plug used prior to the unrolling of the condom may include, for example, the inverted nipple illustrated in FIG. 8, wherein the inverted nipple is substantially aligned with, and plugs the flow of lubricant from, the at least one hole in the lubricant ring rib. In embodiments wherein the inverted nipple or a similar plug is provided by the condom roll, it will be apparent to those skilled in the art that the unrolling of the condom for use will remove the plug from the hole in the lubricant ring rib, thereby allowing for the release of lubricant. Of course, it may be further appreciated that, as discussed hereinthroughout, removal of the plug may not lead to immediate release of the lubricant, but rather the lubricant may remain in situ due to the presence of one or more valves, veins, thin seals, or the like, atop the hole.

It will be further appreciated, particularly in light of the discussion herein with respect to FIG. 8, that the condom roll and ring rib of the condom of the present invention may not only serve to provide a plug for lubricant flow, but additionally may be provided in various locations, or multiple locations, along the shaft of the sheath of the condom, such as to suppress blood flow and thereby enhance performance, and/or to maintain position of the condom during use. More particularly, a known manner of unrolling the condom may be provided, wherein the known roll provides an outer roll, and wherein the rib(s) of the present invention provide a second, or inner, roll that may provide lubricant, plug lubricant, and/or provide an additional pressure ring about the condom.

Figure 9:
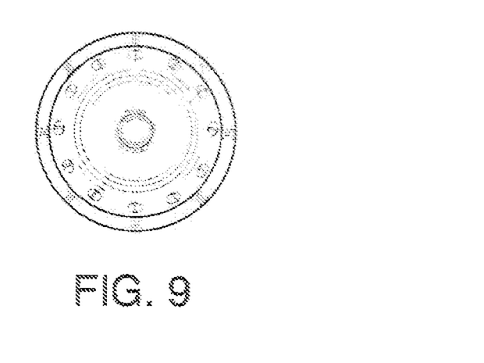
FIG. 9 schematically illustrates a rolled condom in the present invention.

For example, FIG. 9 illustrates an embodiment of the present invention wherein a ring rib of lubricant is provided about the circumference of the condom, and wherein the roll of the condom is provided about the outermost circumference of the lubricant ring about. In the illustrated embodiment, the outer roll of the condom may provide adhesive and/or the aforementioned inverted nipple as a plug for the lubricant. When the condom is unrolled, the lubricant may exit the lubricant ring rib, and further either or both of the lubricant ring rib and the condom roll may be latitudinally moved up or down the shaft of the penis.

Figure 10:
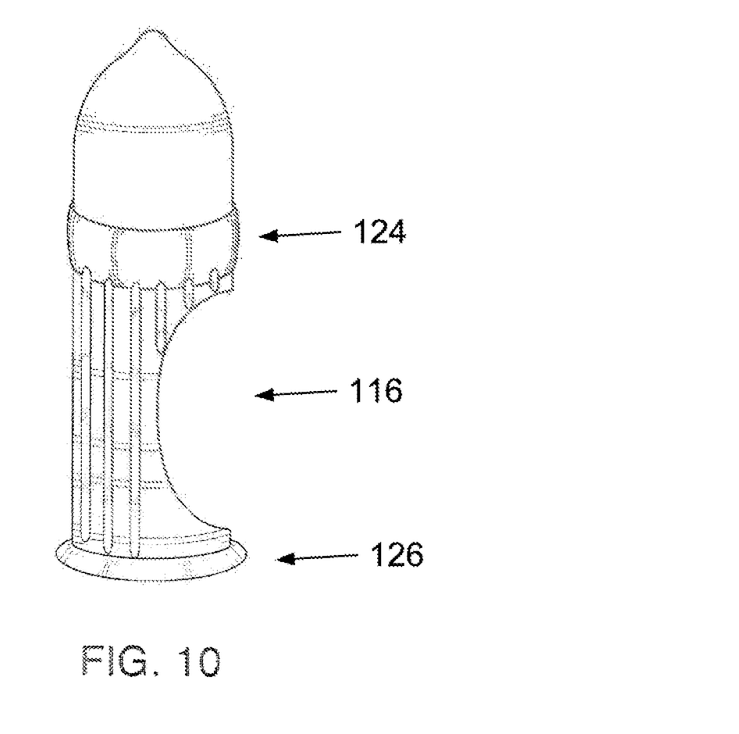
FIG. 10 illustrates a cross-section of the present invention.

Thereby, and as more particularly illustrated in FIG. 10, variations of known condoms may be provided that improve the sexual experience, but that do not increase the likelihood of leakage of bodily fluids. For example, FIG. 10 illustrates the lubricant ring rib 124 of the present invention holding the condom in place at a point approximately halfway down the unrolled condom. As illustrated for example in FIG. 10, one alternative embodiment of a rib 124 may extend in a ring-like manner about the barrel, and may thus be referred to herein as a "ring rib." This ring rib 124 may provide lubricant, and may additionally be used, as illustrated at the base of the unrolled condom in FIG. 10, in conjunction with the prior art roll to further hold the condom in place. It will be noted that the exemplary condom of FIG. 10 includes openings 116 for direct stimulation of the penis latitudinally along the sheath of the condom between the lubricant ring rib 124 and the roll 126, and these openings may be provided because sufficient constrictive pressure is available to hold the condom in place and prevent bodily fluid leakage based on the presence of the lubricant ring rib halfway down the condom shaft.

Figure 11:
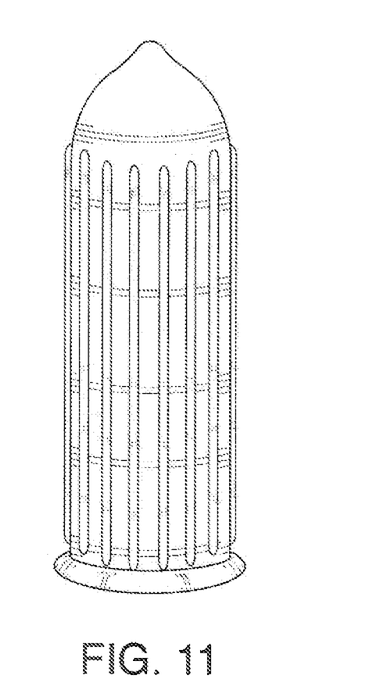
FIG. 11 illustrates a cross-section of the present invention.

FIG. 11 illustrates an additional variation of the lubricant ring rib of the present invention functioning to provide additional pressure to hold the condom in place over and above the prior art condom roll. More specifically, FIG. 11 illustrates the use of vertical reservoir ribs to provide pressure to affix the condom along the penis, as opposed to the horizontal reservoir rib illustrated in certain of the exemplary embodiments hereinabove.

Figure 12:
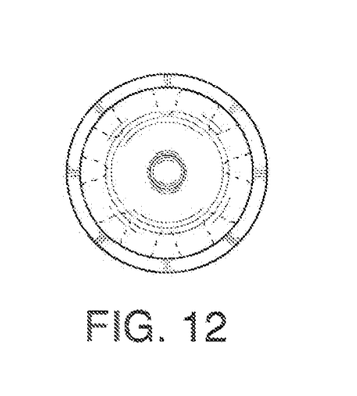
FIG. 12 illustrates a cross-section of the present invention.
Figure 13:
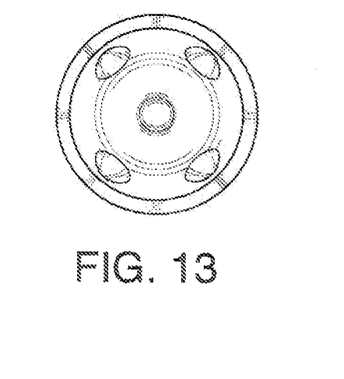
FIG. 13 illustrates a cross-section of the present invention.

FIGS. 12 and 13 illustrate alternative embodiments of horizontal cross sections of the vertical reservoir rib embodiment of FIG. 11. More particularly, FIG. 12 illustrates a cross section of a condom in which the lubricant reservoirs are provided distinct from the condom walls, but inside the outer circumference of the condom. Thereby, the outer circumference of the condom may be substantially circular, but within the circle of the condom's periphery may be lubricant reservoirs that apply additional pressure on the penis within the condom. Nevertheless, the lubricant may be released from these vertical reservoirs by the same means as have been discussed hereinthroughout. Similarly to FIG. 12, FIG. 13 illustrates a cross section wherein the vertical reservoir ribs are outside of a periphery of the condom walls.

Those skilled in the art will appreciate, in light of the discussion herein, that various additional means may be used in order to force lubricant from, or block lubricant within, the lubricant reservoir ribs. Exemplary ones of these means are illustrated in FIGS. 14, 15, 16 and 17.

Figure 14:
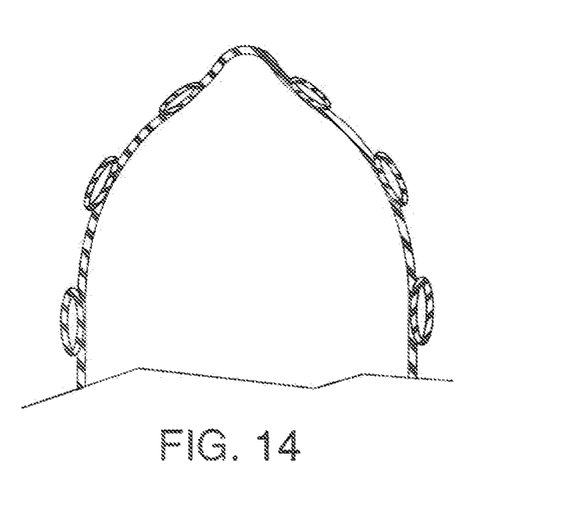
FIG. 14 illustrates a cross-section of the present invention.

More particularly, FIG. 14 illustrates a series of reservoir ribs for lubricant, wherein ones of the series of ribs have differing sizes, heights, lengths, widths, or the like. Variations in pressure along these reservoir ribs of varying size will, if the reservoir ribs include valves, veins, or seals, for example, force lubricant from the reservoir ribs at different times. For example, lubricant may begin to exit the larger reservoir ribs first, and may later exit the smaller reservoir ribs as the larger reservoir ribs empty and the pressure on the smaller reservoirs consequently increases.

Figure 15:
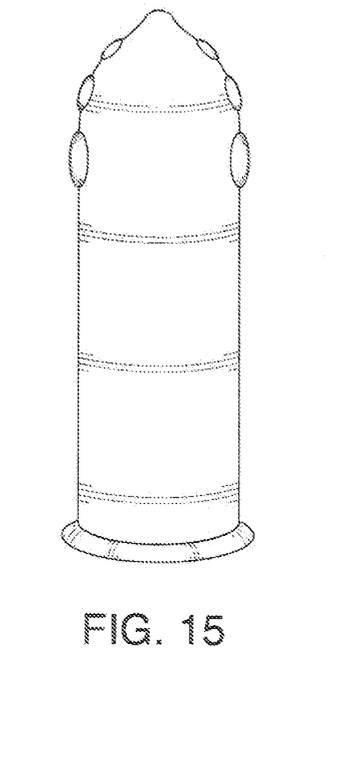
FIG. 15 schematically illustrates a side view the present invention.

FIG. 15 illustrates with particularity that reservoir ribs may be smaller in size, and may be provided as a series of lubricant filled bump ribs along the shaft of the condom. Thereby, as various parts of the condom are inserted, and/or as the pressure upon various parts of the condom increases, different ones of the lubricant bump ribs may be squeezed, may tear, or may pop, and may thereby release the lubricant.

Figure 16:
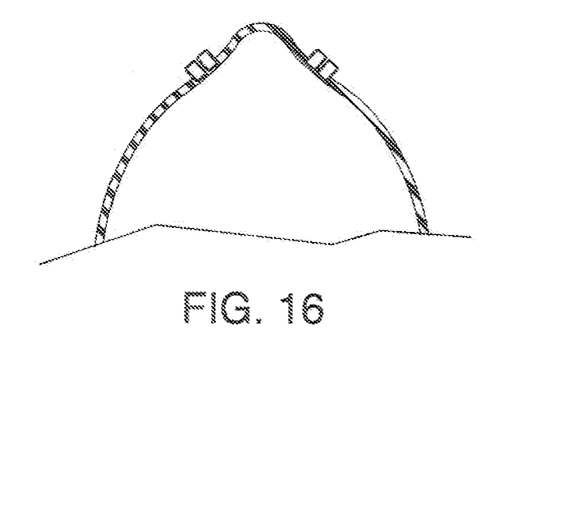
FIG. 16 illustrates a cross-section of the present invention.

FIG. 16 illustrates a two-stage lubricant reservoir rib having a thin seal between the two stages. As illustrated, when pressure is applied to the two-stage reservoir rib, the thin seal will tear, thus releasing lubricant from each stage of the reservoir rib. It will be appreciated by those skilled in the art that this two-stage reservoir rib may have different constituents in each stage, and that the tearing of the seal may thus allow for a mixing of the constituents, such as a mixing of lubricant and spermicide.

Figure 17:
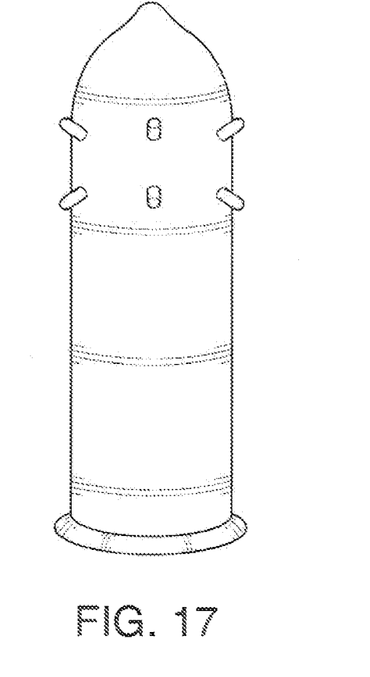
FIG. 17 schematically illustrates a side view the present invention.

FIG. 17 illustrates an embodiment similar to that of FIG. 15, but the embodiment of FIG. 17 illustrates that the lubricant bump ribs may be directionally formed. Thereby, when a force is applied in the opposing phase of the direction of the bump rib, the bump rib may be pulled back, may tear at its base, and lubricant may be consequently released. Of course, the directional bump ribs may be formed in different directions along the same condom shaft, such that certain of the bump ribs may release lubricant upon inward thrust, and others of the bump ribs may release lubricant upon pulling outward. Further, in embodiments such as those discussed above, variations in the size and/or pressure reactivity of the bump ribs may, as illustrated in FIG. 17, allow for release of lubricant both at variable times, and with variable directions of thrust.

Figure 18:
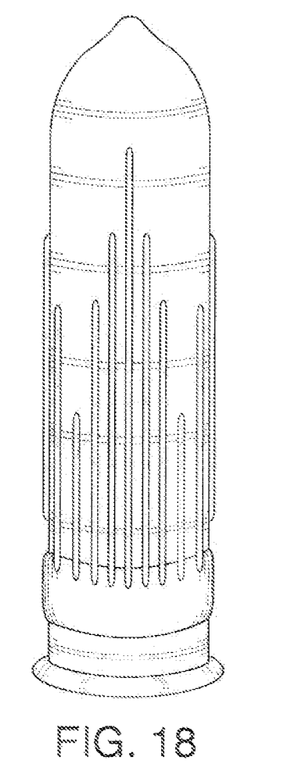
FIG. 18 illustrates a side view of the present invention.

FIG. 18 illustrates an embodiment similar to that of FIG. 1, but the embodiment of FIG. 18 illustrates that the lubricant reservoir may be a singular and uniform open chamber having ribs of varying length extending there from. Thereby, when a force is applied to the laterally placed reservoir, lubricant may be released through the longitudinally deposed ribs. Of course, the number of longitudinally disposed ribs may be formed in different directions along the same condom shaft, such that certain of the ribs may extend to near the distal end of the condom, and certain others may extend only a short distance from the lubricating reservoir. Further, in embodiments such as those discussed above, variations in the size and/or pressure reactivity of the ribs may, as illustrated in FIG. 18, allow for release of lubricant both at variable locations, and in response to variable pressures.

Figure 19:
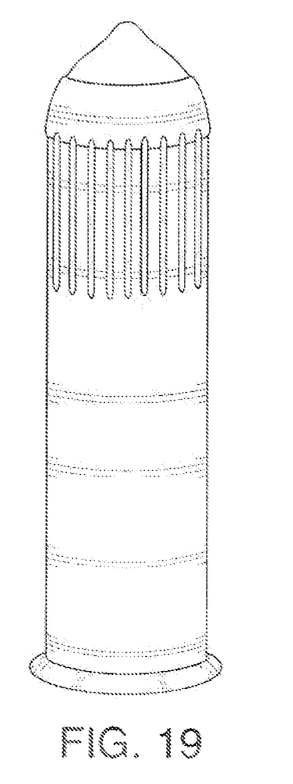
FIG. 19 illustrates a side view of the present invention.

FIG. 19 illustrates an embodiment oppositely disposed compared to that of FIG. 18. Specifically, the lubricant reservoir is located at the distal end, very near the tip of the condom. As explained above, various length ribs may extend away from the reservoir and may extend towards the proximate end of the condom. In addition to varying rib length, ribs, in this embodiment and others, may also be of varying diameter to influence the amount of lubricant available for release through an out flow point, if provided.

Figure 20:
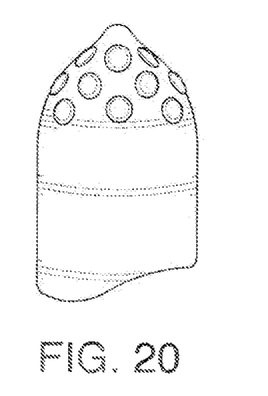
FIG. 20 illustrates a truncated side view of the present invention.

FIG. 20 illustrates the use of small and discrete reservoirs provided in proximity to the distal end of the condom. Each reservoir may contain some volume of lubricant and may include at least one out flow point. In addition to the illustrated uniformity of the individual reservoirs, such reservoirs may be situated in any arrangement to optimize the discharge of lubricant and/or the stimulating effect of the texture provided by the reservoirs. As may be understood by those skilled in the art, the reservoirs may be of varying sizes and may contain varying amounts of lubricant. The lubricant to available reservoir space ratio may also vary to provide rigid to less rigid reservoirs to effect the stimulating effect provided by the reservoirs.

Figure 21:
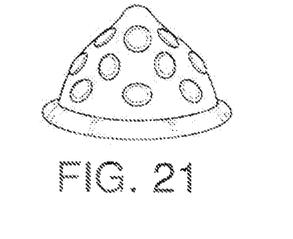
FIG. 21 illustrates a side view of the present invention.

FIG. 21 illustrates an embodiment of FIG. 20 wherein the condom has been rolled from the proximate end. Although not fully rolled for packaging purposes, the illustration shows that even in the rolled state, the external layer(s) of the condom can be easily identified by the user visually and/or tactically by virtue of the raised reservoirs proximate to the distal end.

Figure 22:
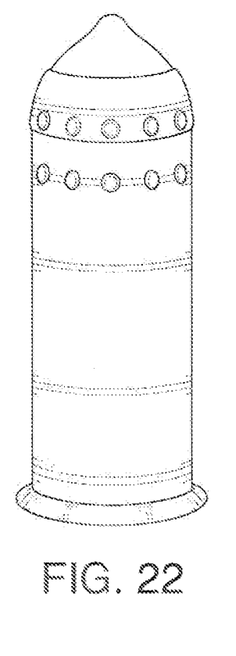
FIG. 22 illustrates a side view of the present invention.

FIG. 22 illustrates a reservoir located near the distal end without covering the end or tip of the condom. The reservoir may include out flow points, as described above, and may be filed with a spermicide, for example, to be of a certain rigidity to optimize the dispensing of lubricant, for example. The out flow points may take any form, and may be female oriented dimples. In addition, male oriented dimples may be provided on the reservoir and/or on the any other portion of the condom exterior, for example, to provide a stimulating affect. Such male dimples may be filled with lubricant, spermicide, air, and/or the condom's primary construction material, for example.

Figure 23:
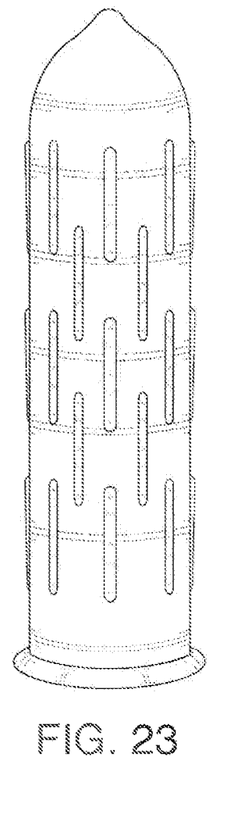
FIG. 23 illustrates a side view of the present invention.

The ribs discussed above may also be arranged in a non-contiguous linear fashion, as illustrated in FIG. 23. Ribs may also be irregular in height and may be angled to increase the pressure and out flow rate of lubricant from such angled ribs. As also illustrated in FIG. 23, angular ribs may be oriented in such a way that the largest end is towards the distal or tip end of the condom, for example, to allow any pressure that may be exerted on the rib to be exerted first on the largest end. In this way, the composition contained in the angled rib may be more fully and quickly extruded from the rib versus from a similarly situated non-angular rib having an overall uniform depth when acted on by the same pressure. As discussed above, the ribs, whether angled or not, may also be of varying widths and depths and may have varying out flow points.

Figure 24:
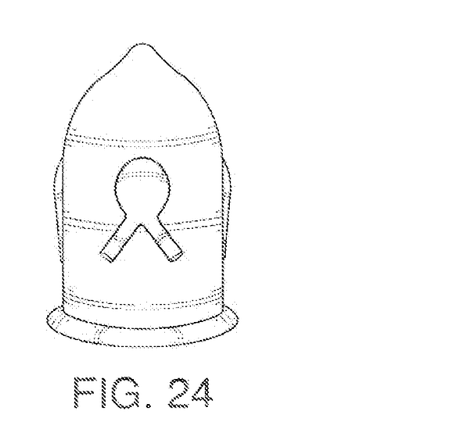
FIG. 24 illustrates a side view of the present invention.
Figure 25:
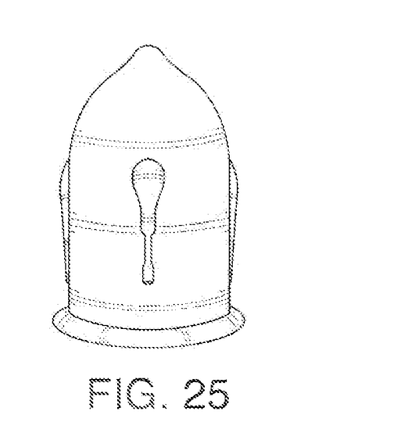
FIG. 25 illustrates a side view of the present invention.
Figure 26:
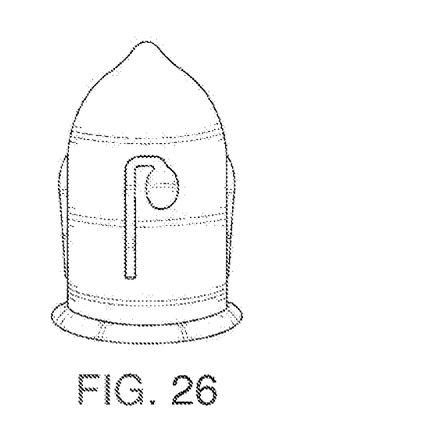
FIG. 26 illustrates a side view of the present invention.

As illustrated in FIG. 24, FIG. 25, and FIG. 26, for example, reservoirs may take any form and may include more than one out flow point. Multiple out flow points may allow for the placement of a greater number of relatively large reservoirs. Such reservoirs, having the same pressure exerted on them as other out flows, such as ribs, for example, may provide a faster transfer of lubricant. Such reservoirs may also provide for increased stimulation and may release any lubrication and/or spermicide in a rate commensurate with the out flow point provided. For example, a small out flow point may be utilized such that the pressure exerted on the reservoir only acts to release a small portion of lubricant, such as, for example, less then 5% of the original total.

Figure 27:
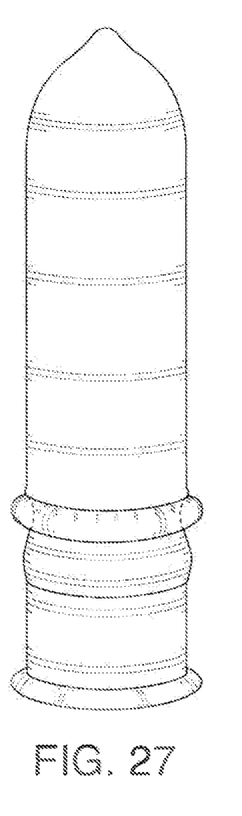
FIG. 27 illustrates a side view of the present invention.

A retaining ring may also be used in conjunction with a reservoir and may act to apply a uniform and consistent pressure on a reservoir regardless of the pressure(s) acting on the condom as a whole. As illustrated in FIG. 27, at least one retaining ring may be disposed against at least one side of the reservoir and may exert force on the reservoir that may be in addition to any pressure(s) that may have been otherwise exerted on the reservoir absent the retaining ring. The retaining ring may have an inner circumference of at least the circumference of the wearer's penis, and an outer circumference greater than the circumference of the reservoir (measured as worn by the wearer).

Figure 28:
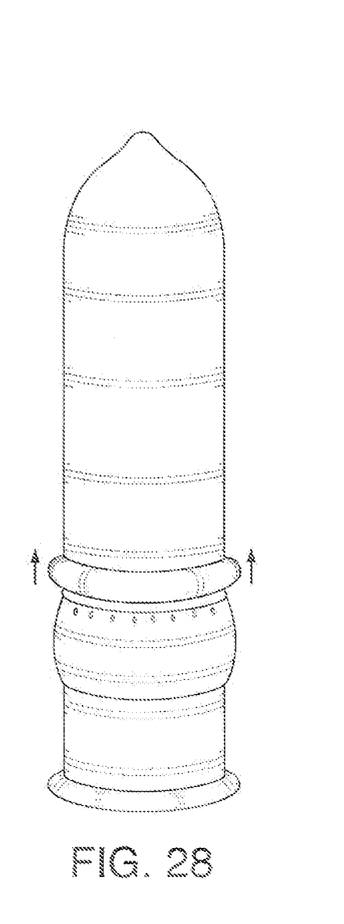
FIG. 28 illustrates a side view of the present invention.

The forward motion of the condom (and the wearer) during use, may allow the retaining ring to exert a force on the reservoir sufficient to extrude the contents of the reservoir through out flow points located thereon. As illustrated in FIG. 28, the out flow points may be located on the leading edge of the reservoir to allow for the contents of the reservoir to be excised towards the distal or tip end of the condom. Further, as illustrated by the ghosted lines in FIG. 28, at least two retaining rings may be used to facilitate pressure on the at least one reservoir. An at least second retaining ring may be proximate to the wearer of the condom and may exert at least one pressure on the at least one reservoir from a side opposite the at least one first ring and at least one out flow point in the reservoir.

Figure 29:
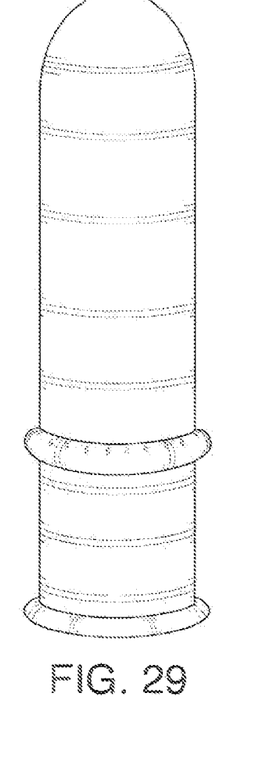
FIG. 29 illustrates a front view of the present invention.

A retaining ring itself may act as a reservoir, may be independent of a condom and may, for example, be used without a condom. As illustrated in FIG. 29, a retaining ring may have out flow points located proximate to the interior circumference and may be on a leading edge of the interior circumference to provide the contents of the reservoir towards the distal or tip end of the condom and/or end of the wearer's penis.

Figure 30:
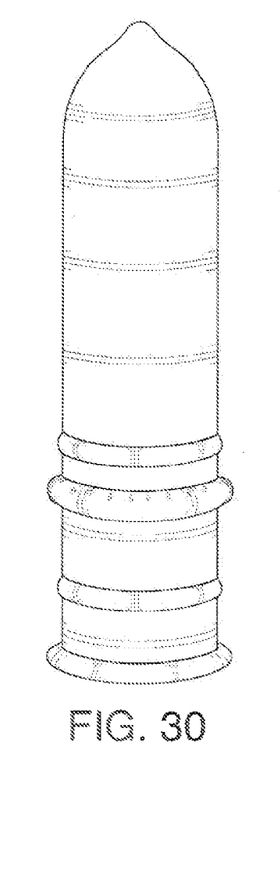
FIG. 30 illustrates a side view of the present invention.

FIG. 30 illustrates an embodiment similar to that of FIG. 28, for example, but the embodiment of FIG. 30 illustrates the use of a retaining ring as a reservoir and illustrates the use of at least one retaining ring acting as a reservoir and at least one retaining ring that is sealed and does not act as a reservoir.

Figure 31:
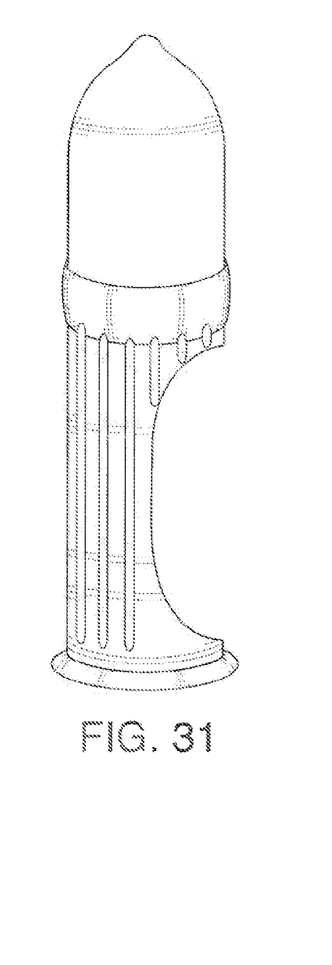
FIG. 31 illustrates a side view of the present invention.

As discussed in more detail above, and as illustrated in FIG. 31, an embodiment of the present invention may provide for the placement of at least one reservoir and/or at least one rib placed around at least one opening in the body of the condom. The placement of the reservoir may be between the opening in the body and the distal or tip end and may include out flow points at the distal and/or proximate end of the reservoir. As discussed above, the contents of the reservoir may also be distributed via ribs which may emanate from the reservoir in either the distal or proximate direction and may vary in length and width, for example, to accommodate the opening in the body of the condom.

Those skilled in the art will appreciate that the embodiments discussed herein provide a significant improvement in the sexual experience. For example, the pressure-based release of lubricant provided in the present invention may allow for release of lubricant on-demand, such as by manual squeezing, thereby preventing interruption of the sexual experience in order to obtain lubrication, and thereby further preventing too much friction or not enough friction during the sexual experience.

The disclosure herein is directed to the variations and modifications of the elements and methods of the invention disclosed that will be apparent to those skilled in the art in light of the disclosure herein. Thus, it is intended that the present invention covers the modifications and variations of this invention, provided those modifications and variations come within the scope of the appended claims and the equivalents thereof.

I claim:

1. A condom comprising:
    a non-porous sheath member having an open end, a closed end and a barrel extending therebetween; and
    at least one rib disposed along said barrel and having an outer portion and an exit pathway through said outer portion, said at least one rib including a multiplicity of unidirectional valve elements housed in serially-distributed fashion therewithin for directing the flow of a lubricant within said rib toward said exit pathway and inhibiting flow of said lubricant within said rib away from said exit pathway.

2. A condom as defined in claim 1 comprising two or more said ribs.

3. A condom as defined in claim 1 in which said exit pathway consists of a plurality of holes.

4. A condom as defined in claim 1 in which said at least one rib extends generally longitudinally from said open end toward said closed end.

5. A condom as defined in claim 1 in which said at least one rib extends in a spiral manner about said barrel.

* * * * *